United States Patent [19]

Yamada et al.

[11] Patent Number: 5,629,456
[45] Date of Patent: May 13, 1997

[54] METHOD OF PREPARING A FLUORENE DERIVATIVE AND THE METHOD OF PURIFYING THEREOF

[75] Inventors: Mitsuaki Yamada, Ibaraki; Katsuhide Okimi, Sakai; Katsuyuki Takahashi; Norio Nagano, both of Osaka, all of Japan

[73] Assignee: Osaka Gas Company Limited, Osaka, Japan

[21] Appl. No.: 350,459

[22] Filed: Dec. 7, 1994

[30] Foreign Application Priority Data

Dec. 10, 1993 [JP] Japan .................... 5-310089

[51] Int. Cl.⁶ .................... C07C 39/12
[52] U.S. Cl. .................... 568/633; 568/631; 568/727
[58] Field of Search .................... 568/633, 631, 568/727

[56] References Cited

U.S. PATENT DOCUMENTS

| | | | |
|---|---|---|---|
| 4,070,392 | 1/1978 | Tresper et al. | 568/631 |
| 4,467,122 | 8/1984 | Szaboles | 568/727 |
| 4,675,458 | 6/1987 | Riemann et al. | 568/727 |
| 4,931,594 | 6/1990 | Knabel et al. | 568/727 |
| 5,248,838 | 9/1993 | Massirio et al. | 568/727 |
| 5,304,688 | 4/1994 | Bowman et al. | 568/727 |

FOREIGN PATENT DOCUMENTS

| | | | |
|---|---|---|---|
| 4-41450 | 2/1992 | Japan | 568/727 |
| 92/07812 | 5/1992 | WIPO | 568/727 |

OTHER PUBLICATIONS

Chen et al, J. Appl. Polymer Sci., vol. 27, pp. 3289–3312 (1982).

Teramoto et al, Chem. Abst, vol. 109, #110, 0492 (1988).

*Primary Examiner*—James H. Reamer
*Attorney, Agent, or Firm*—Larson & Taylor

[57] ABSTRACT

A fluorene derivative of high purity is produced by reacting fluorenone with phenoxyethanol in the presence of a sulfuric acid-thiol catalyst system, dissolving the reaction mixture in a lower aliphatic alcohol and adding water to the resulting solution for precipitation of 9,9-bis(4-(2-hydroxyethoxy) phenyl)fluorene [fluorene derivative]. A fluorene derivative of still higher purity is obtained by recrystallization from a lower aliphatic alcohol.

In accordance with this invention, a fluorene derivative can be produced advantageously on a commercial scale without incurring any appreciable loss of fluorenone, in good yield, with high efficiency and in a reduced production time.

12 Claims, No Drawings

METHOD OF PREPARING A FLUORENE DERIVATIVE AND THE METHOD OF PURIFYING THEREOF

FIELD OF THE INVENTION

This invention relates to a novel method of preparing a fluorene derivative. More particularly, this invention relates to a method of preparing 9,9-bis(4-(2-hydroxyethoxy)phenyl)fluorene which comprises reacting fluorenone with phenoxyethanol in the presence of sulfuric acid and a thiol compound. The invention further relates to a method of purifying crude 9,9-bis(4-(2-hydroxyethoxy)phenyl)fluorene.

9,9-bis(4-(2-Hydroxyethoxy)phenyl)fluorene is a fluorene derivative of the following chemical formula:

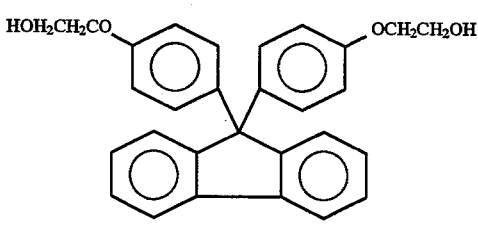

which is of value as a starting compound for the production of epoxy resins and polyesters.

DESCRIPTION OF THE PRIOR ART

It is known that 9,9-bis(4-hydroxyphenyl)fluorene can be synthesized by condensation reaction of fluorenone, as obtained by air oxidation of fluorene in liquid phase, and phenol in the presence of hydrogen chloride-mercaptopropionic acid [J. Appl. Polym. Sci., 27 (9), 3289, 1982] and that 9,9-bis(4-(2-hydroxyethoxy)phenyl)fluorene can also be synthesized by subjecting 9,9-bis(4-hydroxyphenyl)fluorene and ethylene oxide to addition reaction.

However, the above prior art technology starting with fluorenone for the production of 9,9-bis(4-(2-hydroxyethoxy)phenyl)fluorene comprises two production processes. Thus, the prior art technology not only requires the ultimate isolation and purification of the objective compound 9,9-bis(4-(2-hydroxyethoxy)phenyl)fluorene but also requires the separation and purification of the intermediate compound 9,9-bis(4-hydroxyphenyl)fluorene with the associated treatment of unreacted phenol and hydrogen chloride gas in the first process and the treatment of unreacted ethylene oxide in the second process.

The above prior art technology, thus, involves a large number of steps and is, therefore, commercially disadvantageous in terms of production efficiency. Furthermore, the technology involves the use of ethylene oxide which is liable to polymerize chemically, so that the final product tends to contain ethylene oxide polymers.

In a check experiment of the prior art for the production of 9,9-bis(4-(2-hydroxyethoxy)phenyl)fluorene, the inventors of this invention found that the purity and yield of the objective compound were as low as 92.5% and 52.5%, respectively, indicating that this known technology has much to be desired.

The yield values (%) shown in this specification were calculated by the following equation.

Yield (%)=[The number of mols of 9,9-bis(4-(2-hydroxyethoxyphenyl)fluorene]÷[the number of mols of fluorenone in the starting material]×100.

OBJECTS OF THE INVENTION

It is an object of this invention to provide an industrially advantageous technology for preparing a fluorene derivative, i.e. 9,9-bis(4-(2-hydroxyethoxy)phenyl)fluorene, that is to say a method of preparing 9,9-bis(4-(2-hydroxyethoxy)phenyl)fluorene from fluorenone in a single step.

It is another object of this invention to provide a novel production technology for said fluorene derivative which is simplified in respect of the isolation and purification of the reaction product 9,9-bis(4-(2-hydroxyethoxy)phenyl)fluorene.

It is a further object of this invention to provide a simplified technology for the purification of crude 9,9-bis(4-(2-hydroxyethoxy)phenyl)fluorene.

SUMMARY OF THE INVENTION

To overcome the above-mentioned disadvantages of the prior art, the inventors of this invention explored the possibility of synthesizing 9,9-bis(4-(2-hydroxyethoxy)phenyl)fluorene from fluorenone and phenoxyethanol in a single step and, after intensive research, discovered that when the above reaction is conducted in the presence of sulfuric acid and a thiol compound, 9,9-bis(4-(2-hydroxyethoxy)phenyl)fluorene can be produced in good yield, that addition of a lower aliphatic alcohol to the above reaction product mixture for dissolution and the subsequent addition of water to the resulting solution result in precipitation of 9,9-bis(4-(2-hydroxyethoxy)phenyl)fluorene to facilitate its recovery, and that a lower aliphatic alcohol is a good recrystallization solvent for the purification of crude 9,9-bis(4-(2-hydroxyethoxy)phenyl)fluorene. This invention has been developed on the basis of the above findings.

This invention, therefore, relates to a method of preparing a fluorene derivative which comprises reacting fluorenone with phenoxyethanol in the presence of sulfuric acid and a thiol compound to provide 9,9-bis(4-(2-hydroxyethoxy)phenyl)fluorene.

The invention further relates to a method for recovering the fluorene derivative so prepared which comprises adding a lower aliphatic alcohol to the reaction mixture for dissolution and, then, adding water for precipitation of 9,9-bis(4-(2-hydroxyethoxy)phenyl)fluorene.

The invention is further directed to a method of purifying crude 9,9-bis(4-(2-hydroxyethoxy)phenyl)fluorene which comprises recrystallizing the 9,9-bis(4-(2-hydroxyethoxy)phenyl)fluorene from a lower aliphatic alcohol.

DETAILED DESCRIPTION OF THE INVENTION

In accordance with this invention, fluorenone is reacted with phenoxyethanol in the presence of sulfuric acid and a thiol compound which serve as the catalyst. This reaction may be carried out batchwise or continuously. The reaction temperature should be 30°–150° C., preferably 50°–100° C. When the reaction is carried out batchwise, the reaction time should be 1–10 hours, preferably 3–6 hours.

When the reaction temperature is below the above-mentioned range, the rate of reaction tends to decrease to sacrifice the production efficiency. Conversely when the reaction temperature exceeds the above range, the formation of byproducts tends to increase to reduce the yield of the objective compound. When the reaction time is decreased, the unreacted fluorenone tends to increase to sacrifice the yield of the objective compound. When the reaction time is too long, the formation of byproducts is increased to sacrifice the yield of the objective compound.

The concentration of sulfuric acid, which is used as a catalyst in accordance with this invention, should be not less than 75% and preferably not less than 95%. In the practice of this invention, 10–500 ml, preferably 80–200 ml, of sulfuric acid can be advantageously used per mol of fluorenone.

Use of sulfuric acid of lower concentration or in a smaller proportion tends to result in an inadequate catalytic action. Conversely, when the use of an unnecessarily larger amount of sulfuric acid may elicit a sharp temperature buildup to interfere with commercial-sale production, although an increased catalytic action and a reduction in reaction time can be expected.

The method for addition of sulfuric acid to the reaction system is not critical and can be liberally selected with reference to the quantity of the acid to be used and other conditions of the reaction. Taking the batch reaction as an example, it is preferable that the total necessary quantity of liquid sulfuric acid is added dropwise over a period ranging from 15 minutes to 2 hours at a relatively low temperature before the reaction system is brought to the reaction temperature.

The thiol compound which is used as a component of the catalyst system in accordance with this invention appears to act, in the main, as a co-catalyst for the principal catalyst sulfuric acid. The thiol compound which can be used as such a co-catalyst includes, among others, various mercaptans, particularly mercaptans of 1–10 carbon atoms, preferably those of 2–4 carbon atoms, and mercaptocarboxylic acids, particularly mercaptocarboxylic acids of 2–11 carbon atoms, preferably those of 2–4 carbon atoms. Thus, specifically, ethylmercaptan, n-butylmercaptan, 1-octylmercaptan, t-dodecylmercaptan, mercaptoethanol, mercaptoacetic acid and β-mercaptopropionic acid, among others, can be mentioned.

In the practice of this invention, the thiol compound should be used in a proportion of 0.01–100 ml, preferably 0.1–10 ml, to each mol of fluorenone. When a thiol compound with a larger carbon number is used, the reaction tends to be protracted. When the proportion of the thiol compound is too small, the catalytic action tends to be sacrificed. Increasing the proportion of the thiol compound beyond the specified range is not rewarded with the commensurate increase in catalytic effect.

The purities of starting fluorenone and phenoxyethanol are not so critical but from the standpoints of reaction efficiency and ease of purification, both starting materials are preferably of high purity. For example, fluorenone obtained by liquid-phase air oxidation of fluorene derived from coal tar or fluorene obtained as a byproduct in the dealkylation process for the production of benzene can be used as the starting fluorenone.

The starting fluorenone may contain such impurities as acenaphthene, dibenzofuran, biphenyl, methylbiphenyl, etc. but is preferably one with a fluorenone content of not less than 70 weight % and more preferably not less than 90 weight %.

As regards the proportions of fluorenone and phenoxyethanol, generally 2–10 and preferably 3–6 molar equivalents of phenoxyethanol relative to each mol of fluorenone can be used with advantage. When the proportion of phenoxyethanol is smaller than the above range, the formation of byproducts tends to be increased so that the yield of the objective compound is decreased. Increasing the amount of phenoxyethanol too much would cause a decrease of the catalyst concentration to detract from catalytic activity, thus tending to prolong the reaction.

The method for recovery of 9,9-bis(4-(2-hydroxyethoxy) phenyl)fluorene from the reaction mixture at completion of the above reaction between fluorenone and phenoxyethanol is not particularly restricted. A method which is suitable for purposes of this invention comprises adding a lower aliphatic alcohol to the reaction mixture, if necessary with stirring, to prepare a homogeneous solution, adding water to cause precipitation of 9,9-bis(4-(2-hydroxyethoxy)phenyl) fluorene, and recovering the fluorene derivative by, for example, filtration, if necessary followed by drying.

The lower aliphatic alcohol for use as the solvent for the reaction mixture is preferably an aliphatic alcohol of 1–5 carbon atoms and, for still better results, an aliphatic alcohol of 1–3 carbon atoms, such as methanol, ethanol and propanol. For a large-scale operation, methanol which is commercially available at a low price is particularly preferred.

The lower aliphatic alcohol should be used in a proportion of 100–2000 ml, preferably 200–1000 ml, per mol of the fluorene nucleus present in the reaction mixture. When the proportion of the lower aliphatic alcohol is too small, the resulting solution tends to be not fully homogeneous. When the amount of the lower aliphatic alcohol is excessive, an increased amount of water will be needed in the subsequent step. The amount of the water required for precipitating the objective compound is 200–2000 ml, preferably 600–1000 ml, per mol of the fluorene nucleus present in the reaction mixture.

Referring to the purification technology for further purification of the recovered reaction product, i.e. the crude 9,9-bis(4-(2-hydroxyethoxy)phenyl)fluorene, thus produced, a recrystallization technology using a lower aliphatic alcohol, i.e. an aliphatic alcohol containing 1–5 carbon atoms, preferably 1–3 carbon atoms, is suitable as the recrystallization solvent. The lower aliphatic alcohol which can be used for recrystallization of the recovered reaction product includes methanol, ethanol and propanol, among other solvents. For a large-scale operation, methanol which is commercially available at a low price is preferred.

The above-mentioned lower aliphatic alcohol to be added as the recrystallization solvent should be used in a proportion of 200–5000 ml, preferably 800–3500 ml, to each mol of the fluorene nucleus contained in the recovered reaction product. While the specific method and conditions of recrystallization are not particularly restricted, a recommended exemplary method comprises adding said lower aliphatic alcohol to the crude reaction product and, after dissolution under heating, causing a precipitate to separate out under stirring at ambient temperature or under external cooling with cooling water, and separating the precipitate by filtration and drying the same.

The purification method according to this invention is particularly suited for converting the crude compound of about 85–92% purity to a pure compound of not less than 94%, preferably not less than 95% and, more preferably, not less than 98% purity.

EFFECTS OF THE INVENTION

In accordance with this invention, 9,9-bis(4-(2-hydroxyethoxy)phenyl)fluorene can be advantageously produced from fluorenone on a commercial scale without incurring any appreciable loss of fluorenone, in good yield, with improved efficiency and in a reduced production time.

Furthermore, in accordance with this invention, the 9,9-bis(4-(2-hydroxyethoxy)phenyl)fluorene produced by the reaction of fluorenone with phenoxyethanol can be easily isolated from the reaction mixture.

In addition, by the purification method according to this invention, 9,9-bis(4-(2-hydroxyethoxy)phenyl)fluorene of high purity can be obtained by the simple procedure of recrystallization.

EXAMPLES

Example 1

A 1-liter reactor equipped with a stirrer, cooling pipe and burette was charged with 45 g (0.25 mol) of fluorenone of 99.5 wt. % purity (obtained by liquid phase air oxidation of fluorene) and 138 g (1.00 mol) of phenoxyethanol (tradename: PHE-G, Yokkaichi Gosei, Co., Ltd.) followed by addition of 0.2 ml of β-mercaptopropionic acid. Then, 40 ml of 95% sulfuric acid was added dropwise over 30 minutes. The reaction was continued at a constant temperature of 50° C. for 5 hours for completion.

After completion of the reaction, 100 ml of methanol was added and the mixture was stirred for 1 hour. Then, 150 ml of pure water was added for precipitation of the reaction product. After cooling to ambient temperature, the system was filtered to separate the precipitate.

This precipitate was recrystallized from 800 ml of methanol. Thus, methanol was added to the recovered precipitate and after dissolution by heating, a crystal crop is caused to separate out under stirring at ambient temperature or, if necessary, under external cooling with cooling water. The resulting crop was recovered by filtration and dried.

The purity of the resulting compound 9,9-bis(4-(2-hydroxyethoxy)phenyl)fluorene was 98.7 weight % and the yield was 81.5 g or 73.8%.

Example 2

The same reactor as used in Example 1 was charged with 45 g (0.25 mol) of fluorenone of 99.5 wt. % purity and 121 g (0.88 mol) of phenoxyethanol (tradename: PHE-G, Yokkaichi Gosei, Ltd.) followed by addition of 0.2 ml of β-mercaptopropionic acid. Then, 45 ml of 95% sulfuric acid was added dropwise over 45 minutes. The reaction was further continued at a constant temperature of 65° C. for 4 hours for completion.

After completion of the reaction, the reaction mixture was cooled to 50° C., added with 100 ml of methanol, and stirred for 1 hour. Then, 200 ml of pure water was added to cause precipitation of the reaction product. After cooling to ambient temperature, the precipitate was recovered by filtration. This precipitate was recrystallized from 800 ml of methanol.

The purity of this compound [9,9-bis(4-(2-hydroxyethoxy)phenyl)fluorene] was 96.9 wt. % and the yield was 84.1 g or 74.8%.

Example 3

The same reactor as used in Example 1 was charged with 45 g (0.25 mol) of fluorenone of 99.5 wt. % purity and 138 g (1.00 mol) of phenoxyethanol (tradename: PHE-G, Yokkaichi Gosei, Ltd.) followed by addition of 0.2 ml of β-mercaptopropionic acid. Then, 60 ml of 95% sulfuric acid was added over 45 minutes and the reaction was further continued at a constant temperature of 65° C. for 5 hours for completion.

After completion of the reaction, the reaction mixture was cooled to 50° C., diluted with 100 ml of methanol, and stirred for 1 hour. Then, 200 ml of pure water was added for precipitation of the reaction product and, after cooling to ambient temperature, the product was separated by filtration. This solid product was recrystallized from 800 ml of methanol.

The purity of this product compound [9,9-bis(4-(2-hydroxyethoxy)phenyl)fluorene] was 94.9 wt. % and the yield was 79.6 g or 68.6%.

Example 4

The same reactor as used in Example 1 was charged with 45 g (0.25 mol) of fluorenone of 99.5 wt. % purity and 138 g (1.00 mol) of phenoxyethanol followed by addition of 0.5 ml of 1-octylmercaptan. Then, 50 ml of 95% sulfuric acid was added dropwise over 50 minutes and the reaction was further continued at a constant temperature of 65° C. for 6 hours for completion.

After completion of the reaction, the reaction mixture was cooled to 50° C., diluted with 100 ml of methanol and stirred for 1 hour. Then, 200 ml of pure water was added to cause precipitation of the reaction product. After cooling to ambient temperature, the precipitate was recovered by filtration. This precipitate was recrystallized from 800 ml of methanol.

The purity of this compound [9,9-bis(4-(2-hydroxyethoxy)phenyl)fluorene] was 96.9 wt. % and the yield was 72.1 g or 64.1%.

Comparison Example 1

A 1-liter reactor equipped with a stirrer, cooling pipe and gas inlet pipe was charged with 45 g (0.25 mol) of fluorenone of 99.5 wt. % purity and 138 g (1.00 mol) of phenoxyethanol followed by addition of 0.2 ml of β-mercaptopropionic acid. While the reaction temperature was maintained at 65° C., hydrogen chloride gas was introduced at a flow rate of 100 ml/min. for 180 minutes. The reaction was further continued for 5 hours.

Analysis of a small sample of the reaction product mixture revealed that only 3% of fluorenone had been converted to 9,9-bis(4-(2-hydroxyethoxy)phenyl)fluorene. After completion of the reaction, the reaction mixture was cooled to 50° C. and the residual hydrogen chloride gas was removed by nitrogen gas purging. Then, the reaction mixture was diluted with 100 ml of methanol and stirred for 1 hour. Thereafter, 200 ml of pure water was added and the mixture was cooled to ambient temperature. No precipitate was obtained, however.

The above results indicate that as the catalyst for use in the production of 9,9-bis(4-(2-hydroxyethoxy)phenyl)fluorene from fluorenone and phenoxyethanol, the combination of the specified acid and thiol compound according to this invention is preferred to the hydrogen chloride-mercaptopropionic acid system which is a known catalyst for condensation of fluorenone with phenol.

What is claimed is:

1. A method of preparing a fluorene derivative which comprises reacting fluorenone with phenoxyethanol to synthesize 9,9-bis(4-(2-hydroxyethoxy)phenyl)fluorene at 30°–150° C. using as a catalyst, per mol of fluorenone, 80–200 ml of sulfuric acid of not less than 75% concentration and 0.1–10 ml of at least one thiol compound selected from the group consisting of ethylmercaptan, n-butylmercaptan, 1-octylmercaptan, t-dodecylmercaptan, mercaptoethanol, mercaptoacetic acid and β-mercaptopropionic acid.

2. The method of preparing a fluorene derivative as claimed in claim 1 wherein said fluorenone is one containing not less than 70 weight % of fluorenone as obtained by liquid-phase air oxidation of fluorene derived from coal tar or byproduct fluorene from a dealkylation process for the production of benzene.

3. The method of preparing a fluorene derivative as claimed in claim 1 wherein sulfuric acid of not less than 95% concentration is used in a proportion of 10–500 ml to each mol of fluorenone.

4. The method of preparing a fluorene derivative as claimed in claim 1 wherein the thiol compound is at least one member selected from the group consisting of ethylmercaptan, n-butylmercaptan, 1-octylmercaptan, t-dodecylmercaptan, mercaptoethanol, mercaptoacetic acid and β-mercaptopropionic acid.

5. The method of preparing a fluorene derivative as claimed in claim 1 wherein 9,9-bis(4-(2-hydroxyethoxy)phenyl)fluorene is recovered from the reaction mixture obtained by the reaction of fluorenone with phenoxyethanol by adding a lower aliphatic alcohol to the reaction mixture for dissolution and adding water to the resulting solution for precipitation of 9,9-bis(4-(2-hydroxyethoxy)phenyl)fluorene for recovery.

6. The method of preparing a fluorene derivative as claimed in claim 5 wherein the lower aliphatic alcohol to be added to the reaction mixture is an aliphatic alcohol of 1–5 carbon atoms.

7. The method of preparing a fluorene derivative as claimed in claim 5 wherein the lower aliphatic alcohol to be added to the reaction mixture is an aliphatic alcohol of 1–3 carbon atoms.

8. The method of preparing a fluorene derivative as claimed in claim 5 wherein the lower aliphatic alcohol is added in a proportion of 100–2000 ml to each mol of the fluorene nucleus contained in the reaction mixture.

9. The method of preparing a fluorene derivative as claimed in claim 5 wherein the lower aliphatic alcohol is added in a proportion of 200–1000 ml to each mol of the fluorene nucleus contained in the reaction mixture.

10. The method of preparing a fluorene derivative as claimed in claim 5 wherein water is used in a proportion of 200–2000 ml to each mol of the fluorene nucleus contained in the reaction mixture.

11. The method of preparing a fluorene derivative as claimed in claim 5 wherein water is used in a proportion of 600–1000 ml to each mol of the fluorene nucleus contained in the reaction mixture.

12. The method of preparing a fluorene derivative as claimed in claim 1 further comprising adding 100–2000 ml of a lower aliphatic alcohol per mol of the fluorene nucleus contained in the reaction mixture as obtained by the reaction of fluorenone with phenoxyethanol and, then, adding 200–2000 ml of water to the resulting solution for precipitation of 9,9-bis(4-(2-hydroxyethoxy)phenyl)fluorene for recovery.

* * * * *